(12) United States Patent
McClure et al.

(10) Patent No.: US 8,386,048 B2
(45) Date of Patent: Feb. 26, 2013

(54) SYSTEMS AND METHODS FOR COMMUNICATING WITH OR PROVIDING POWER TO AN IMPLANTABLE STIMULATOR

(75) Inventors: Kelly H. McClure, Simi Valley, CA (US); Scott M. Loftin, Rosamond, CA (US); Robert D. Ozawa, Woodland Hills, CA (US); Michael L. Fister, Simi Valley, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1601 days.

(21) Appl. No.: 11/034,190

(22) Filed: Jan. 11, 2005

(65) Prior Publication Data

US 2005/0119716 A1 Jun. 2, 2005

Related U.S. Application Data

(63) Continuation-in-part of application No. 10/609,449, filed on Jun. 27, 2003.

(60) Provisional application No. 60/392,475, filed on Jun. 28, 2002.

(51) Int. Cl.
*A61N 1/378* (2006.01)
(52) U.S. Cl. ............... 607/60; 607/61; 607/32; 607/31
(58) Field of Classification Search .................. 607/32, 607/33, 60, 61
See application file for complete search history.

(56) References Cited

U.S. PATENT DOCUMENTS

| | | | |
|---|---|---|---|
| 5,193,539 A | 3/1993 | Schulman et al. | |
| 5,193,540 A | 3/1993 | Schulman et al. | |
| 5,312,439 A | 5/1994 | Loeb | |
| 5,314,453 A * | 5/1994 | Jeutter | 607/61 |
| 5,405,367 A | 4/1995 | Schulman et al. | |
| 5,545,191 A * | 8/1996 | Mann et al. | 607/57 |
| 5,750,926 A | 5/1998 | Schulman et al. | |
| 5,755,748 A * | 5/1998 | Borza | 607/61 |
| 6,051,017 A | 4/2000 | Loeb et al. | |

(Continued)

FOREIGN PATENT DOCUMENTS

| | | |
|---|---|---|
| WO | WO-97/1885 A1 | 5/1997 |
| WO | WO-00/01320 A2 | 1/2000 |

(Continued)

OTHER PUBLICATIONS

Cameron, et al., "Micromodular Implants to Provide Electrical Stimulation of Paralyzed Muscles and Limbs", IEEE Transactions on Biomedical Engineering, vol. 44, No. 9, (Sep. 1997), pp. 781-790.

(Continued)

*Primary Examiner* — Joseph Stoklosa
(74) *Attorney, Agent, or Firm* — Wong, Cabello, Lutsch, Rutherford, & Brucculeri, LLP (57) ABSTRACT

An exemplary system for communicating with or providing power to an implantable stimulator includes a coil configured to emit a magnetic field for driving a corresponding circuit in the implantable stimulator and a coil driver circuit configured to drive the coil with a tuning frequency. The coil driver circuit actively adjusts the tuning frequency such that the coil operates at a frequency substantially equal to a resonant frequency. An exemplary method of communicating with or providing power to an implantable stimulator includes driving a coil with a tuning frequency and actively adjusting the tuning frequency such that the coil operates at a frequency substantially equal to a resonant frequency. The coil emits a magnetic field used to drive a corresponding circuit in the implantable stimulator.

6 Claims, 12 Drawing Sheets

U.S. PATENT DOCUMENTS

| | | | |
|---|---|---|---|
| 6,061,596 | A | 5/2000 | Richmond et al. |
| 6,164,284 | A | 12/2000 | Schulman et al. |
| 6,175,764 | B1 | 1/2001 | Loeb et al. |
| 6,181,965 | B1 | 1/2001 | Loeb et al. |
| 6,185,452 | B1 | 2/2001 | Schulman et al. |
| 6,185,455 | B1 | 2/2001 | Loeb et al. |
| 6,208,894 | B1 | 3/2001 | Schulman et al. |
| 6,214,032 | B1 | 4/2001 | Loeb et al. |
| 6,259,937 | B1 | 7/2001 | Schulman et al. |
| 6,315,721 | B2 | 11/2001 | Schulman et al. |
| 6,553,263 | B1 | 4/2003 | Meadows et al. |
| 6,567,703 | B1 | 5/2003 | Thompson et al. |
| 6,591,139 | B2 * | 7/2003 | Loftin et al. .................... 607/60 |
| 7,225,032 | B2 * | 5/2007 | Schmeling et al. ............. 607/61 |
| 2003/0234631 | A1 * | 12/2003 | Schulman et al. ............ 318/677 |
| 2004/0088012 | A1 * | 5/2004 | Kroll et al. ........................ 607/9 |

FOREIGN PATENT DOCUMENTS

| | | | |
|---|---|---|---|
| WO | WO-00/01320 | A3 | 1/2000 |

OTHER PUBLICATIONS

Loeb, et al., ANorth Sea: Transducers and Electrodes—Injectable Microstimulator for Functional Electrical Stimulation@, Med. & Biol. Eng. & Computer, North Sea Special Feature, 29 (Nov. 1991), pp. NS13-NS19.

Loeb, at al., ABIONTM Bionic Neurons for Functional and Therapeutic Electrical Stlmulation@, 20th Annual International Conference of IEEE Engineering in Medicine and Biology ABiomedical Engineering Towards the Year 2000 and Beyond@, Oct. 29-Nov. 1, (1998), Hong Kong, 5 pages.

\* cited by examiner

SYSTEMS AND METHODS FOR COMMUNICATING WITH OR PROVIDING POWER TO AN IMPLANTABLE STIMULATOR

RELATED APPLICATIONS

The present application is a continuation-in-part application of U.S. application Ser. No. 10/609,449, filed Jun. 27, 2003, which application claims the benefit of Provisional Application Ser. No. 60/392,475, filed Jun. 28, 2002. Both applications are incorporated herein by reference in their entireties.

BACKGROUND

Radio-frequency (RF) powered implantable stimulators and battery powered implantable stimulators are described in the art. See, for instance, U.S. Pat. No. 5,193,539 ("Implantable Microstimulator); U.S. Pat. No. 5,193,540 ("Structure and Method of Manufacture of an Implantable Microstimulator"); U.S. Pat. No. 5,312,439 ("Implantable Device Having an Electrolytic Storage Electrode"); U.S. Pat. No. 6,185,452 ("Battery-Powered Patient Implantable Device"); U.S. Pat. Nos. 6,164,284 and 6,208,894 (both titled "System of Implantable Device for Monitoring and/or Affecting Body Parameters"). Each of these patents is incorporated herein by reference in its respective entirety.

Implantable stimulators configured to prevent or treat various disorders associated with prolonged inactivity, confinement or immobilization of one or more muscles are taught, e.g., in U.S. Pat. No. 6,061,596 ("Method for Conditioning Pelvis Musculature Using an Implanted Microstimulator"); U.S. Pat. No. 6,051,017 ("Implantable Microstimulator and Systems Employing the Same"); U.S. Pat. No. 6,175,764 ("Implantable Microstimulator System for Producing Repeatable Patterns of Electrical Stimulation"); U.S. Pat. No. 6,181,965 ("Implantable Microstimulator System for Prevention of Disorders"); U.S. Pat. No. 6,185,455 ("Methods of Reducing the Incidence of Medical Complications Using Implantable Microstimulators"); and U.S. Pat. No. 6,214,032 ("System for Implanting a Microstimulator"). Each of these patents is incorporated herein by reference in its respective entirety.

A typical implantable stimulator is intended to permanently remain in the body of a patient once it is implanted. Hence, transcutaneous communication between an implantable stimulator and an external device may be important for the stimulator to function properly. For example, communication with the implantable stimulator may be effected to perform a number of functions including, but not limited to, transferring power to the stimulator, transferring data to and from the stimulator, programming the stimulator, and monitoring the stimulator's various functions.

SUMMARY

In one of many possible embodiments, the present invention provides a system and method for communicating with or providing power to an implantable stimulator. An exemplary system includes a coil configured to emit a magnetic field for driving a corresponding circuit in the implantable stimulator and a coil driver circuit configured to drive the coil with a tuning frequency. The coil driver circuit actively adjusts the tuning frequency such that the coil operates at a frequency substantially equal to a resonant frequency.

An exemplary method of communicating with or providing power to an implantable stimulator includes driving a coil with a tuning frequency and actively adjusting the tuning frequency such that the coil operates at a frequency substantially equal to a resonant frequency. The coil emits a magnetic field used to drive a corresponding circuit in the implantable stimulator.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

Several types of implantable stimulators and external devices utilize a magnetic field to achieve transcutaneous communication. An implantable stimulator and an external device may both have an RF coil that is used as the transmitter and receiver of the magnetic field. Depending on the application, the coupling coefficient between the RF coils may be extremely poor. Hence, the external device's RF coil and the transmitted magnetic field strength may be relatively large. A relatively large transmitted magnetic field strength may cause the communication system between an implantable stimulator and an external device to be sensitive to detuning effects such as changes in the geometry and position of the RF coils, proximity of the RF coils to metal objects, and variability of implantation depth of the stimulator in the body. Such detuning effects may result in significant loss in magnetic field strength, which, in turn, may cause the implantable stimulator to malfunction.

Hence, systems and methods for facilitating communication and/or power transfer between an external device and an implantable stimulator are described herein. An external device may include a coil configured to emit a magnetic field that is used to drive a corresponding circuit in the implantable stimulator and a coil driver circuit configured to drive the coil with a tuning frequency. The coil driver circuit may be configured to actively adjust the tuning frequency such that the coil operates at a frequency substantially equal to the coil's resonant frequency.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1:
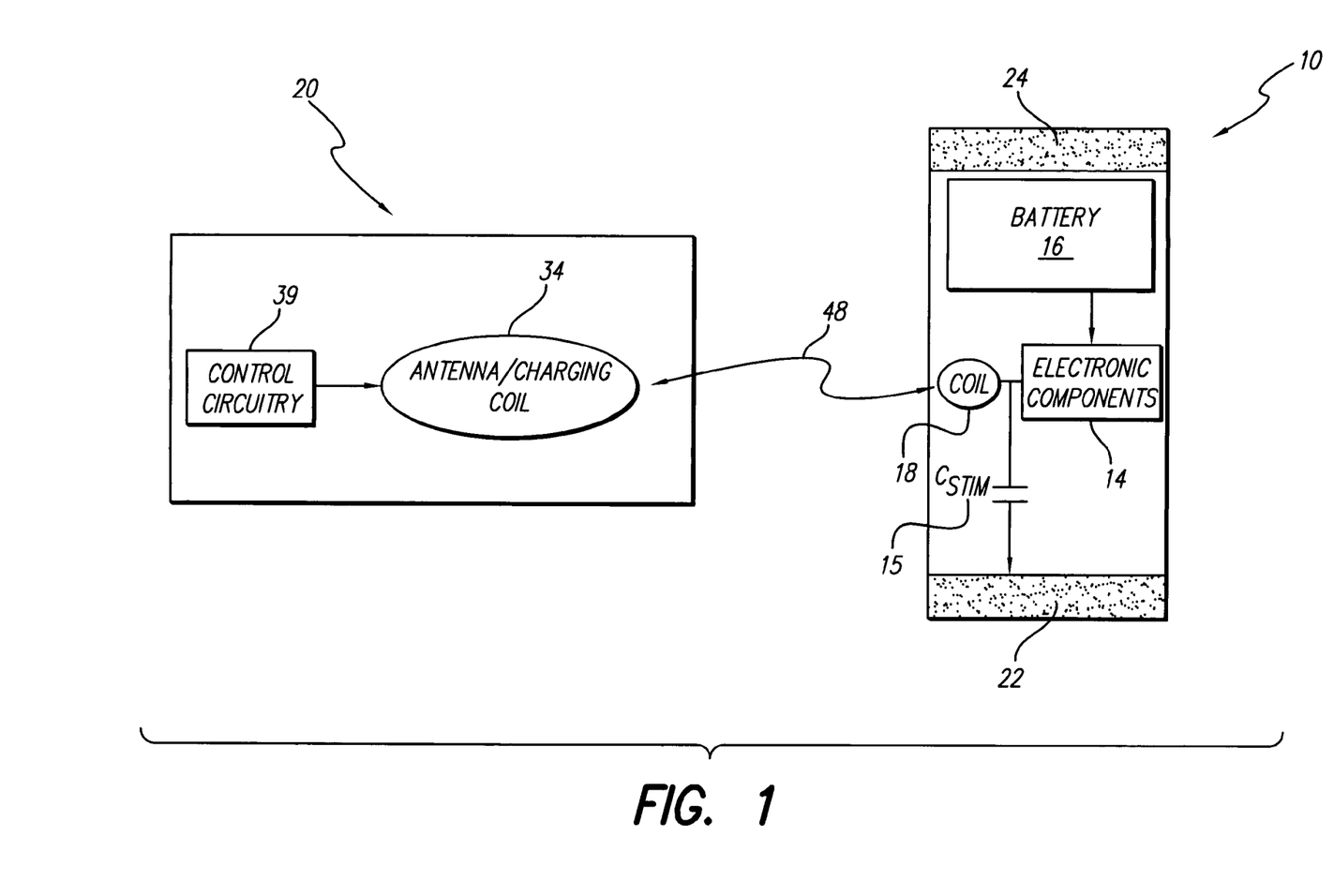
FIG. 1 shows an exemplary implantable stimulator and an exemplary external device according to principles described herein.

FIG. 1 shows an exemplary implantable stimulator (10) and an exemplary external device (20). The implantable stimulator (10) may be any type of implantable medical device. For example, the implantable stimulator (10) may be an implantable microstimulator. Microstimulators are smaller than conventionally sized stimulators and are more easily implanted in a patient. Microstimulators may be injected through a large bore needle or placed via a small incision in the skin. An exemplary, but not exclusive, implantable microstimulator is the BION® microstimulator (Advanced Bionics® Corporation, Valencia, Calif.) which may be configured to stimulate tissue to alleviate urinary incontinence, reduce pain, or otherwise provide therapy for various disorders. Other examples of implantable stimulators include, but are not limited to, spinal cord stimulators (SCS), cochlear implants, and deep brain stimulators. As used herein and in the appended claims, unless otherwise specifically denoted, the terms "stimulator" and "microstimulator" will be used interchangeably to refer to any implantable medical device that may be implanted within a patient and configured to transcutaneously communicate with an external device.

The implantable stimulator (10) may be implanted in the target tissue area of a patient and the external device (20) may be used to communicate with the stimulator (10). Such communication may include, but is not limited to, transcutaneously transmitting data to the stimulator (10), receiving data from the stimulator (10), transferring power to the rechargeable battery (16) in the stimulator (10), and/or providing recovery power to the rechargeable battery (16) when the battery has been depleted to zero volts.

As illustrated in FIG. 1, the stimulator (10) may include a number of components including a rechargeable battery (16) configured to supply the stimulator (10) with power, a coil (18) configured to receive and/or emit a magnetic field that is used to communicate with the external device (20), a stimulating capacitor (15), and two or more electrodes (22, 24) configured to stimulate tissue with current. One or more of these components may be housed within a case (not shown). The stimulator (10) may include additional and/or different electronic components (14) configured to perform a variety of functions as best serves a particular application.

The exemplary external device (20) of FIG. 1 may include control circuitry (39) and an antenna/charging coil (34) configured to emit and/or receive a magnetic field that is used to communicate with the implantable stimulator (10). In one embodiment, the antenna/charging coil (34) and the stimulator's coil (18) communicate via a bidirectional telemetry link (48). The bidirectional telemetry link (48) is also known as a frequency shift key (FSK) telemetry link or as an RF telemetry link. The components of the external device (20) will be described in more detail below.

The external device (20) may be configured to perform any number of functions. For example, the external device (20) may be configured to transcutaneously charge the rechargeable battery (16) in the implanted stimulator (10). The external device (20) may also be configured to transcutaneously transmit data to the stimulator (10), receive data from the stimulator (10), and/or provide recovery power to the rechargeable battery (16) when the battery has been depleted to zero volts. The transmitted data may include configuration bits, programming bits, calibration bits, and/or other types of data. The signals that are sent between the external device (20) and the stimulator (10) may be modulated using frequency shift keying (FSK), on-off keying (OOK), or any other type of modulation scheme.

The functions performed by the external device (20) will vary as best serves the particular application of the stimulator (10). The shape and design of the external device (20) will likewise vary. For example, in one embodiment, the external device (20) may comprise a chair pad and a base station. In use, the chair pad may be placed on a chair and a patient who has an implanted stimulator (10) may sit on the chair pad to recharge the battery (16) in the stimulator (10) and to transfer data between the chair pad and the stimulator (10). Alternatively, the external device (20) may be housed within a casing that is worn by the patient near the surface of the skin. The external device may be also include a remote control configured to send programming information to the implantable stimulator (10). In general, the external device (20) may be any device configured to communicate with an implantable stimulator (10).

Figure 2:
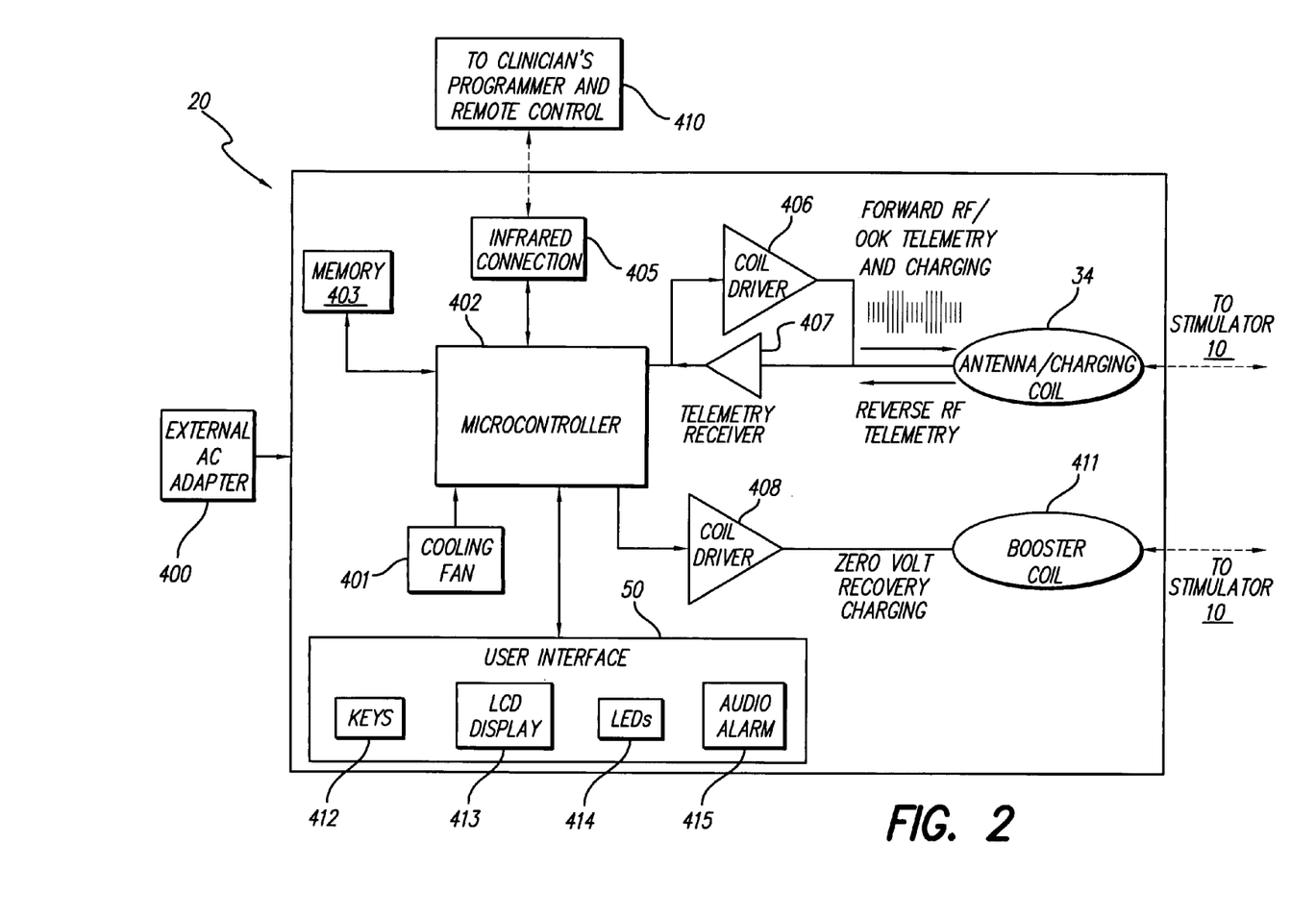
FIG. 2 is a functional block diagram of an exemplary external device according to principles described herein.

FIG. 2 is a functional block diagram of an exemplary external device (20) according to one embodiment. As shown in FIG. 2, the external device (20) may include a number of components, some or all of which are configured to facilitate the transfer of power and/or data to the implantable stimulator (10). For example, the illustrated external device (20) may include memory (403), one or more coils (34, 411), one or more coil driver circuits (406, 408), a user interface (50), and a microcontroller (402). The microcontroller (402) is configured to control the operation of the various components included in the external device (20). A cooling fan (401) may be included to cool the microcontroller (402). The external device (20) may be powered, for example, by an external alternating current (AC) adapter (400). Alternatively, the external device may be powered by a battery or by some other power source.

As shown in FIG. 2, the user interface (50) may include user input keys (412), one or more LCD displays (413), one or more LED displays (414) and/or an audio alarm (415). These controls may assist a user in controlling the external device (20) and/or the stimulator (10). The audio alarm (415) may be used to indicate to the user when the external device (20) has finished charging the stimulator's battery (16; FIG. 1), for example. The audio alarm (415) may also be used as a signal indicator for any other system event or mode.

As mentioned, the external device (20) may include a coil driver circuit (406) configured to control the operation of the antenna/charging coil (34). The coil driver circuit (406) will be described in more detail below. In some embodiments, the external device (20) may include a second coil driver circuit (408) configured to control the operation of a second coil (411). The second coil (411) may be configured provide recovery power to the rechargeable battery (16) of an implanted stimulator when the battery has been depleted down to zero volts. In other words, the second coil (411) may be configured to provide zero volt recovery (ZVR) for the rechargeable battery (16). The second coil (411) is also known as a booster coil.

The external device (20) may further include a receiver (407) configured to receive reverse telemetry signals from the implantable stimulator (10). These signals may then be processed by the microcontroller (402). Furthermore, the microcontroller (402) may communicate with an external clinician programmer (410) and/or a remote control (410) via an infrared connection (405) or any other type of connection.

Figure 3:
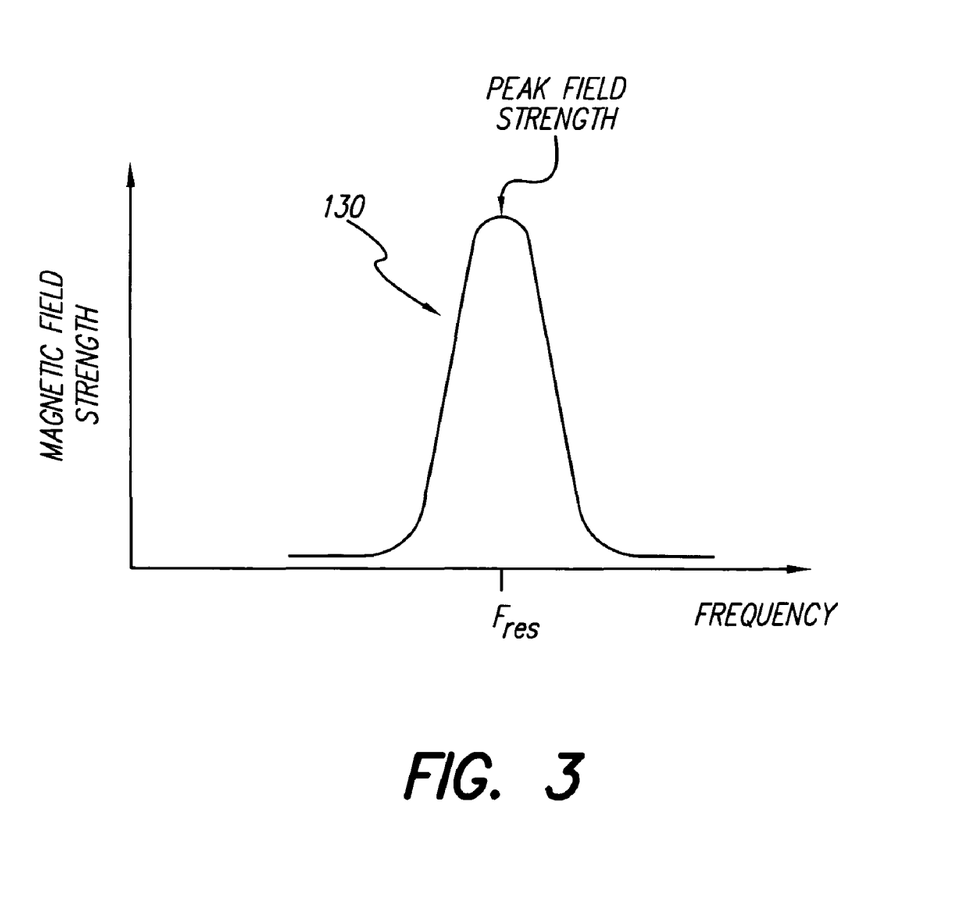
FIG. 3 is a graphical representation of the magnetic field strength versus tuning frequency of an antenna/charging coil.

The antenna/charging coil (34) often has a high quality (Q) factor. In other words, the antenna/charging coil (34) is most efficient when being driven by the coil driver circuit (406) within a narrow range of driving frequencies. The "resonant frequency" of a coil is the frequency at which the coil is the most efficient, i.e., the frequency at which the coil outputs the highest magnetic field strength with the least amount of current applied to the coil. FIG. 3 is a graphical representation of the antenna/charging coil's (34) magnetic field strength (130) versus tuning frequency. As shown in FIG. 3, the magnetic field strength (130) is at a maximum at a resonant frequency $f_{res}$. Hence, the antenna/charging coil (34; FIG. 1) is most efficient when being driven at the resonant frequency $f_{res}$.

However, the resonant frequency $f_{res}$ of the antenna/charging coil (34) may be variable and may constantly shift in response to a number of factors. For example, a change in the distance between the antenna/charging coil (34) and the implantable stimulator (10) may cause the resonant frequency to shift. Other factors such as the variability of implantation depth of the stimulator (10) in the body and changes in the physical, electrical, and/or magnetic properties of the antenna/charging coil (34) and/or other components in the external device (20) may also cause the resonant frequency to shift to the right or the left along the frequency axis of FIG. 3. Such detuning effects may result in significant loss in magnetic field strength, which, in turn, may significantly decrease the efficiency of the antenna/charging coil (34).

Figure 4:
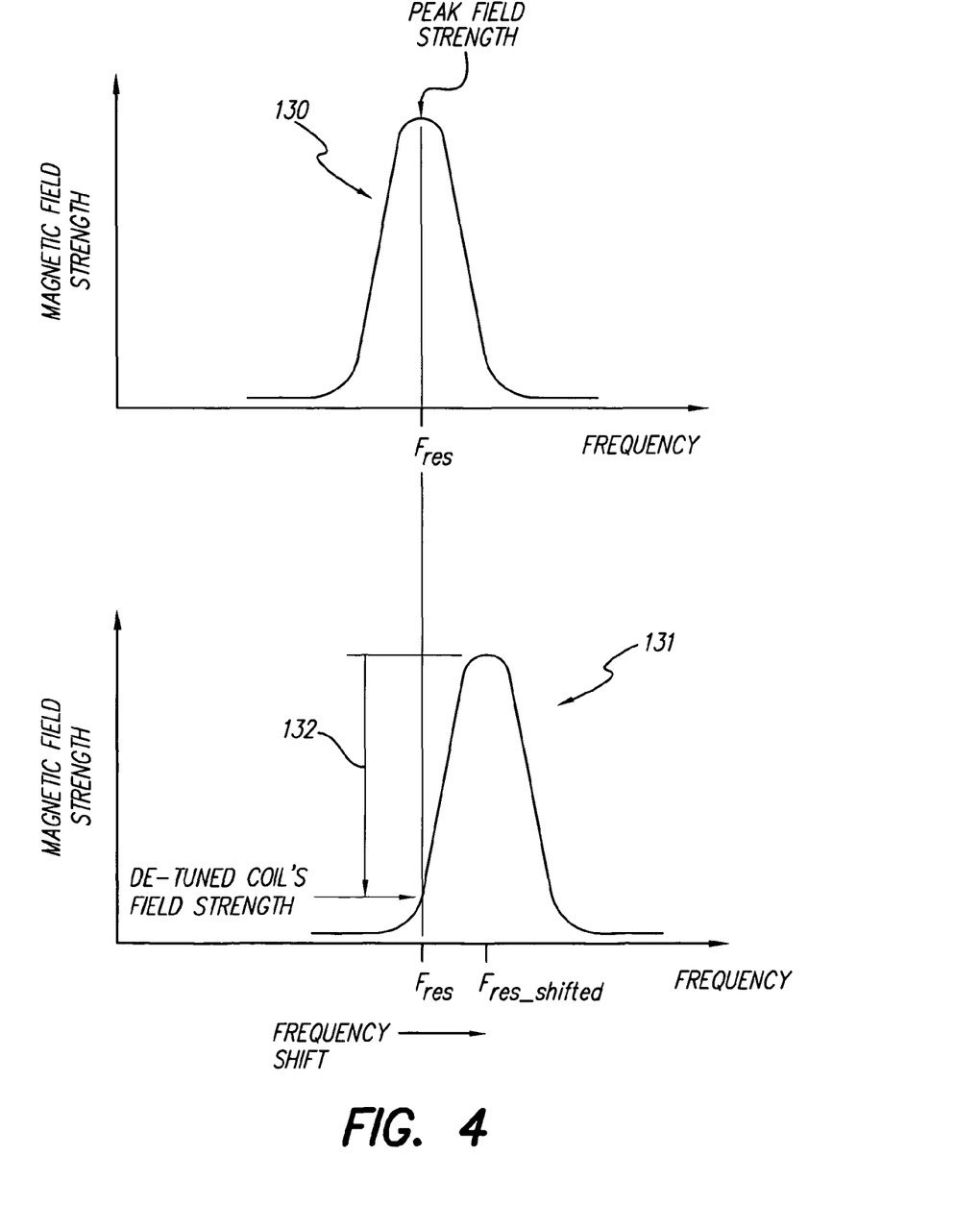
FIG. 4 shows the effect of a shift in the resonant frequency on the efficiency of an antenna/charging coil.

FIG. 4 shows the effect of a shift in the resonant frequency on the antenna/charging coil's (34) efficiency. FIG. 4 shows two curves. The top curve (130) shows that the magnetic field strength of the antenna/charging coil (34) is at a maximum if the resonant frequency is equal to $f_{res}$. The bottom curve (131) shows the effect of a shift in the resonant frequency on the magnetic field strength of the antenna/charging coil (34). As shown in FIG. 4, the resonant frequency has been shifted from $f_{res}$ to $f_{res\_shifted}$ for the bottom curve (131). However, the tuning frequency of the antenna/charging coil (34) is still equal to $f_{res}$, the original resonant frequency, resulting in a significant drop (132) in the magnetic field strength of the antenna/charging coil (34).

Figure 5:
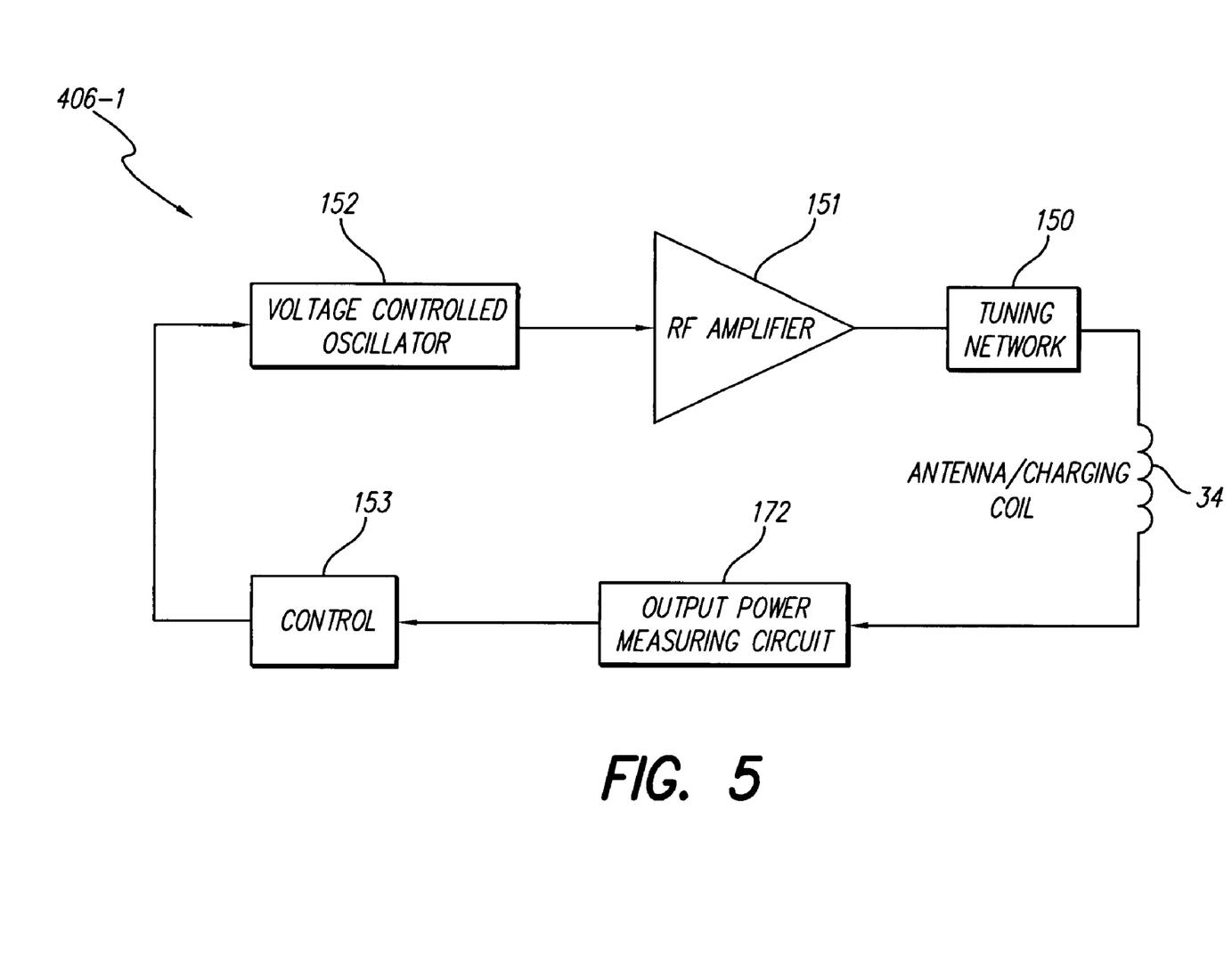
FIG. 5 illustrates an exemplary coil driver circuit configured to actively adjust the tuning frequency of the antenna/charging coil according to principles described herein.

In one embodiment, the external device (20) is configured to actively tune or adjust the tuning frequency of the antenna/charging coil (34) such that the antenna/charging coil (34) operates at a frequency substantially equal to the resonant frequency. The tuning frequency is also known as the driving frequency. FIG. 5 illustrates an exemplary coil driver circuit (406-1) configured to actively adjust the tuning frequency of the antenna/charging coil (34). As shown in FIG. 5, the coil driver circuit (406-1) may include a tuning network (150), an amplifier (151), a voltage controlled oscillator (VCO) (152), a control function (153), and an output power measuring circuit (172). The components of the coil driver circuit (406-1) shown in FIG. 5 are merely illustrative of many different combinations of components that may be used to actively adjust the tuning frequency of the antenna/charging coil (34).

In some embodiments, the tuning network (150) may include one or more electrical components such as a tuning capacitor, inductor, and/or a combination of resistors. As shown in FIG. 5, the tuning network (150) may be driven by an RF amplifier (151). In some embodiments, the output power measuring circuit (172) is configured to measure the output power of the antenna/charging coil (34) and may be any circuit known in the art for measuring the output power of the antenna/charging coil (34). As previously illustrated, if the antenna/charging coil (34) becomes detuned due to a shift in the resonant frequency, the magnetic field strength of the antenna/charging coil (34) decreases. A decrease in the magnetic field strength of the antenna/charging coil (34) corresponds to a decrease in the output power of the antenna/charging coil (34).

The output power of the antenna/charging coil (34) is proportional to the square of the current flowing through the antenna/charging coil (34). Any change in current flowing through the antenna/charging coil (34) results in a corresponding change in the output power of the antenna/charging coil (34). Thus, the output power measuring circuit (172) may be configured to measure the current flowing through the antenna/charging coil (34) to determine the output power of the antenna/charging coil (34). As used herein and in the appended claims, any circuit configured to measure the output power of a coil or the actual power delivered to a coil may perform such measurement by measuring the current flowing through the coil or by any other method of measuring power known in the art.

In the illustrated example, the output power measuring circuit (172) is configured to output a signal representing a value of the measured output power to a control function (153). The control function (153) is configured to detect a change in the measured output power and cause the VCO (152) to adjust the input frequency into the amplifier (151) such that the antenna/charging coil (34) is constantly being driven at the resonant frequency. For example, if there is a shift in the resonant frequency of the antenna/charging coil (34), the control function (153) will detect the corresponding drop in output power of the antenna/charging coil (34). The control function (153) may then cause the VCO (152) to increase or decrease the frequency that is input into the amplifier (151). The input frequency into the amplifier (151) is adjusted until the control function (153) determines that the output power of the antenna/charging coil (34) is maximized.

In various embodiments, the control function (153) may include analog, digital, and/or software components. For example, the control function (153) may be realized using an integrated circuit (IC), a processor with firmware, an application specific integrated circuit (ASIC), a field programmable gate array (FPGA), a digital signal processor (DSP), a software program, and/or any other combination of hardware and/or software.

Figure 6:
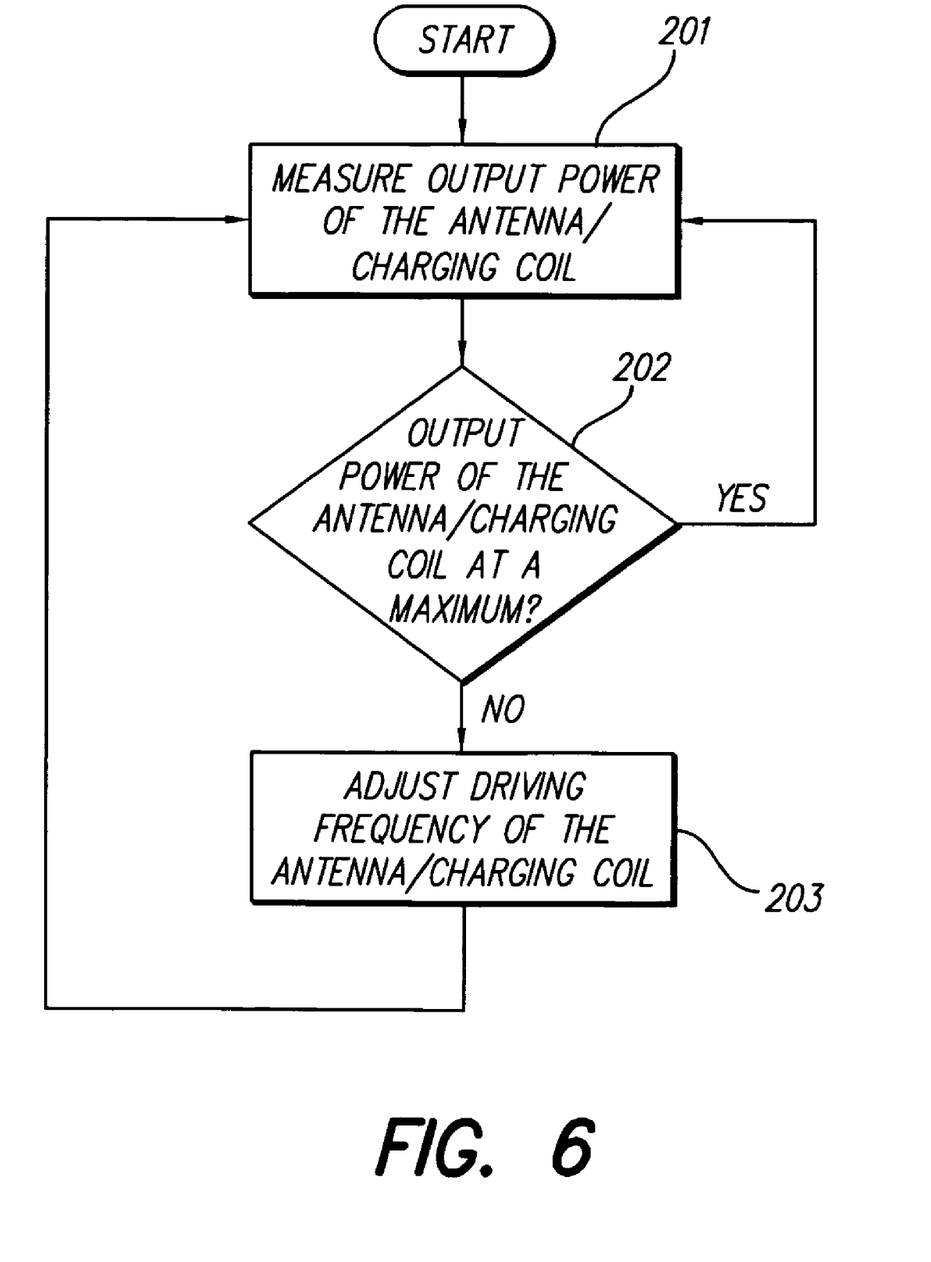
FIG. 6 is a flow chart illustrating an exemplary method of actively adjusting the tuning frequency of the antenna/charging coil such that the antenna/charging coil operates at a frequency substantially equal to the resonant frequency according to principles described herein.

FIG. 6 is a flow chart illustrating an exemplary method of actively adjusting the tuning frequency of the antenna/charging coil (34) such that the antenna/charging coil (34) operates at a frequency substantially equal to the resonant frequency. As shown in FIG. 6, the output power of the antenna/charging coil (34) is first measured (step 201) and reported to the control function (153). The control function (153) may then determine whether the output power of the antenna/charging coil (34) is at a maximum (step 202), i.e., the antenna/charging coil (34) is being driven at its resonant frequency. If the measured output power is not maximized (No; step 202), the control function (153) may cause the VCO (152) to adjust the tuning frequency of the antenna/charging coil (34) (step 203). In one embodiment, the tuning frequency is adjusted by decreasing or increasing the frequency of the signal input into the amplifier (151) that drives the antenna/charging coil (34). As shown in FIG. 6, this process may be repeated until the control function (153) determines that the output power of the antenna/charging coil (34) is at a maximum (Yes; step 202).

Figure 7:
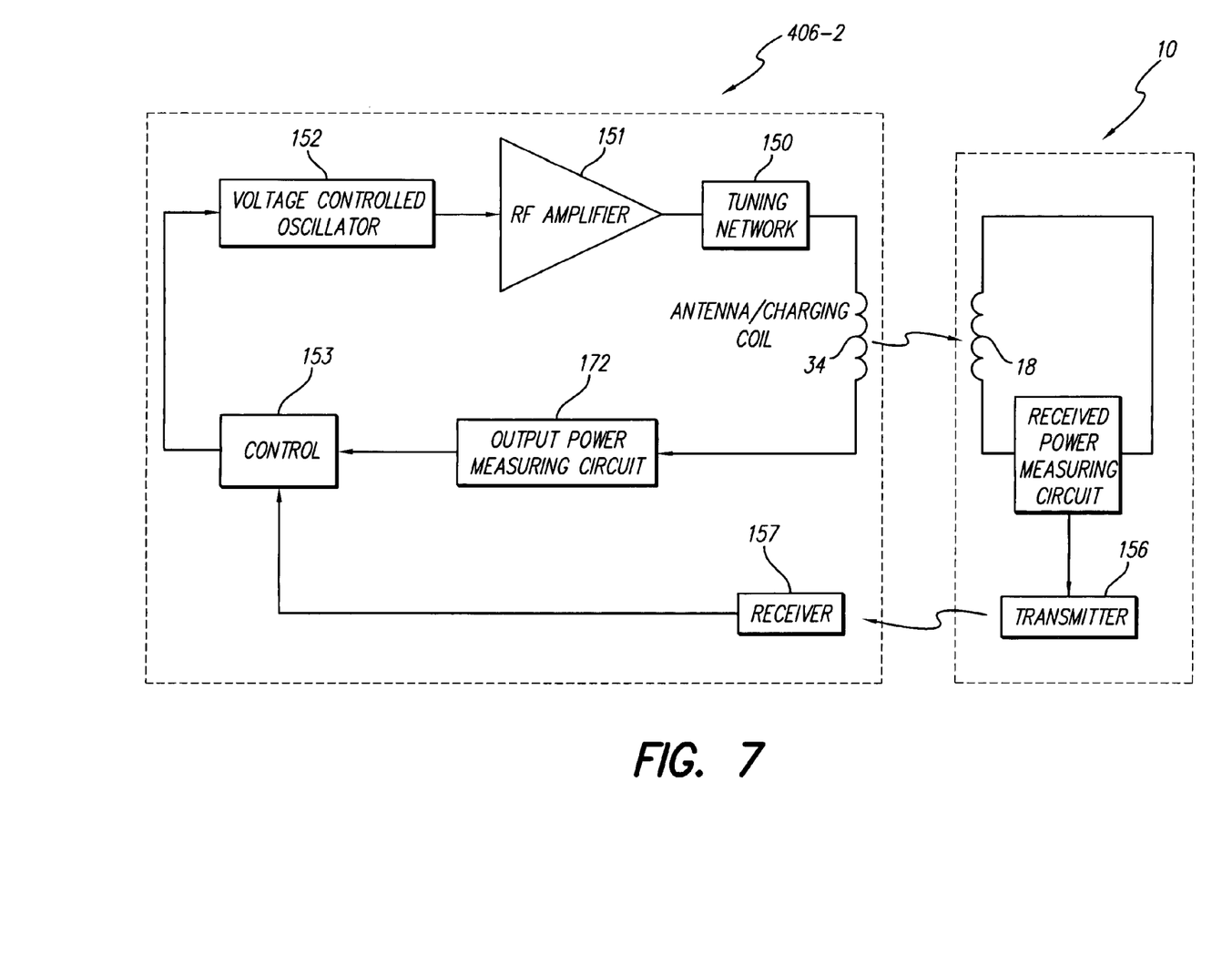
FIG. 7 illustrates an alternative exemplary coil driver circuit and an internal stimulator configured to actively adjust the tuning frequency of the antenna/charging coil according to principles described herein.

FIG. 7 illustrates an alternative exemplary coil driver circuit (406-2) configured to actively adjust the tuning frequency of the antenna/charging coil (34). Like the coil driver circuit (406-1) of FIG. 5, the coil driver circuit (406-2) includes a tuning network (150), an amplifier (151), a voltage controlled oscillator (VCO) (152), a control function (153), and an output power measuring circuit (172) configured to measure the output power of the antenna/charging coil (34). However, in the illustrated example, the control function (153) is further configured to receive a signal comprising a measured value of the actual power delivered to the receiving coil (18) of the implantable stimulator (10). Hence, as shown in FIG. 7, the implantable stimulator (10) may include a received power measuring circuit (155) configured to measure the actual power delivered to the receiving coil. As mentioned above, the received power measuring circuit (155) may be configured to measure the current flowing through the receiving coil (18) to determine the actual power delivered to the receiving coil (18). The implantable stimulator (10) includes a transmitter (156) configured to wirelessly transmit the signal comprising the measured value of the actual power delivered to the receiving coil (18) to the control function (153). The coil driver circuit (406-2) includes a receiver circuit (157) configured to receive the transmitted signal.

Hence, the control function (153) may further optimize the tuning frequency output by the VCO (152) by analyzing both the output power of the antenna/charging coil (34) and the actual power delivered to the receiving coil (18) of the stimulator (10). The control function (153) may then compare the actual power delivered to the receiving coil (18) with the output power of the antenna/charging coil (34). The control function (153) may then cause the VCO (152) to adjust the tuning frequency that is input into the amplifier (151) such that the actual power transfer between the external device (20) and the stimulator (10) is maximized as demonstrated by the current induced in the receiving coil (18) and measured by the received power measuring circuit (155) of the stimulator (10). In an alternative embodiment (not shown), the control function (153) controls the VCO (152) based only on the actual power delivered to the receiving coil (18).

Figure 8:
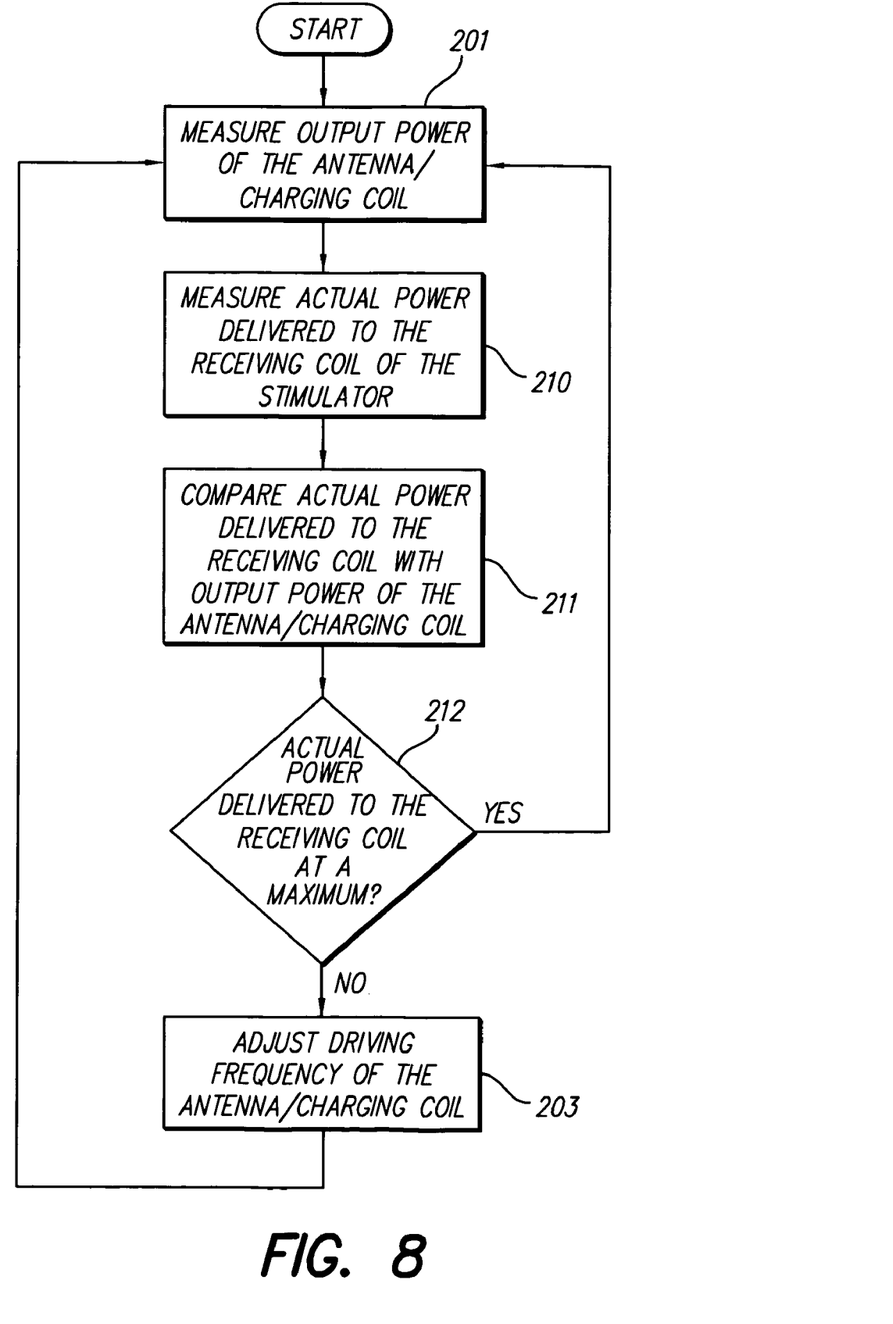
FIG. 8 is a flow chart illustrating an exemplary method of actively adjusting the tuning frequency of the antenna/charging coil such that the antenna/charging coil operates at a frequency substantially equal to the resonant frequency according to principles described herein.

FIG. 8 is a flow chart illustrating an exemplary method of actively adjusting the tuning frequency of the antenna/charging coil (34) such that the antenna/charging coil (34) operates at a frequency substantially equal to the resonant frequency. As shown in FIG. 8, the output power of the antenna/charging coil (34) is first measured (step 201) and reported to the control function (153). The actual power delivered to the receiving coil (18) of the stimulator (10) is also measured (step 210) and reported to the control function (153). The control function (153) may then compare the actual power delivered to the receiving coil (18) with the output power of the antenna/charging coil (step 211). Based on this comparison, the control function (153) may cause the VCO (152) to adjust the tuning frequency of the antenna/charging coil (34) (step 203) if the actual power delivered to the receiving coil is not at a maximum (No; step 212). For example, the tuning frequency is adjusted by decreasing or increasing the frequency of the signal input into the amplifier (151) that drives the antenna/charging coil (34). As shown in FIG. 8, this process may be repeated until the control function (153) determines that the actual power delivered to the receiving coil (18) is at a maximum (Yes; step 212).

Figure 9:
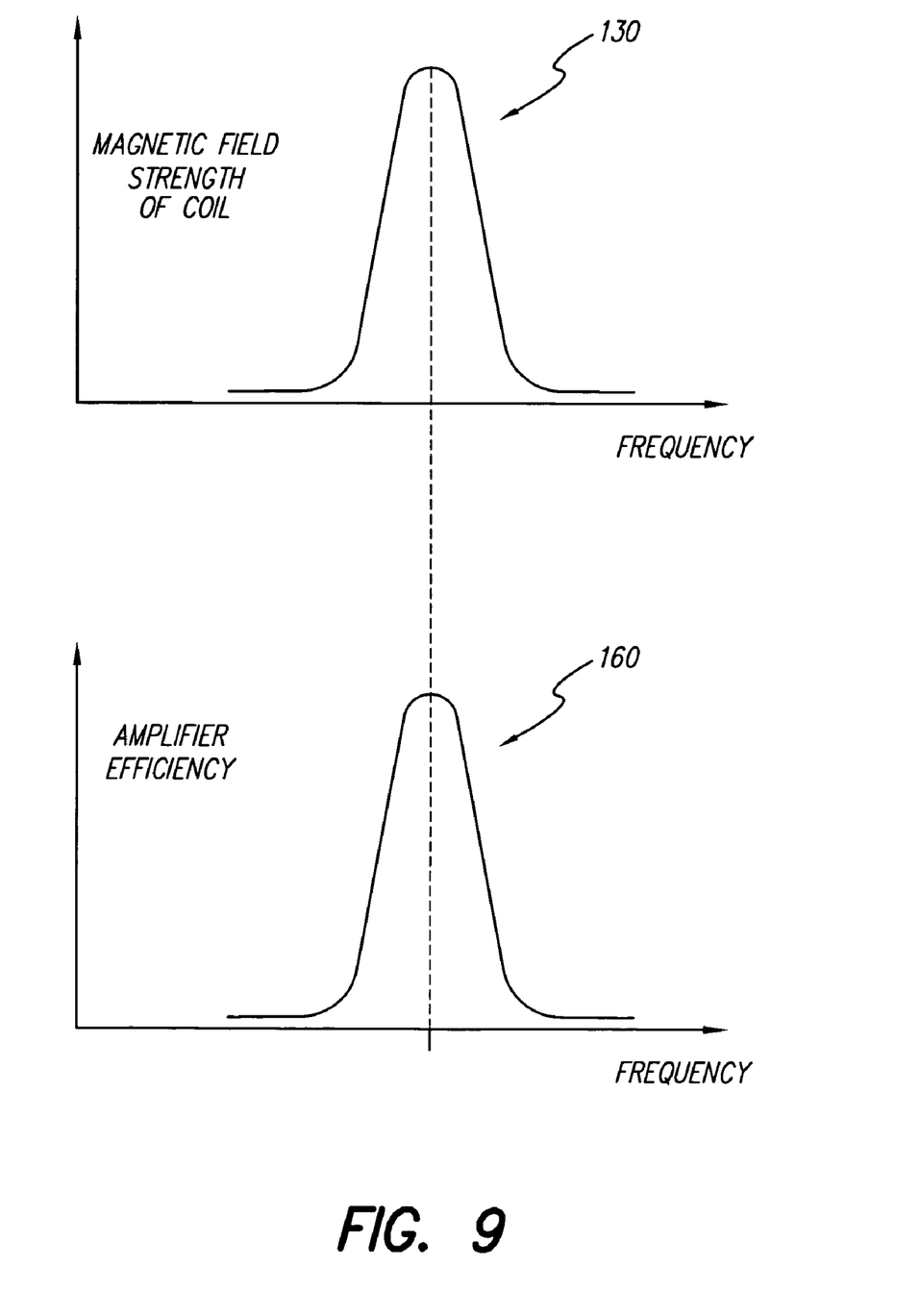
FIG. 9 illustrates the relationship between the efficiency of the amplifier and the magnetic field strength curve of the antenna/charging coil according to principles described herein.

In some embodiments, the coil driver circuit (406; FIG. 2) may be configured to adjust the tuning frequency of the antenna/charging coil (34) by maximizing the efficiency of the amplifier (151). The efficiency of the amplifier may be defined as the ratio of the output power delivered to the antenna/charging coil (34) to the power input to the amplifier (151). FIG. 9 illustrates the relationship between the efficiency of the amplifier (151) and the magnetic field strength of the antenna/charging coil (34). As shown in FIG. 9, the curve (160) representing the efficiency of the amplifier (151) may have the same basic shape as the magnetic field strength curve (130) of the antenna/charging coil (34). Hence, the antenna/charging coil (34) may be tuned to operate at the resonant frequency by maximizing the efficiency of the amplifier (151).

Figure 10:
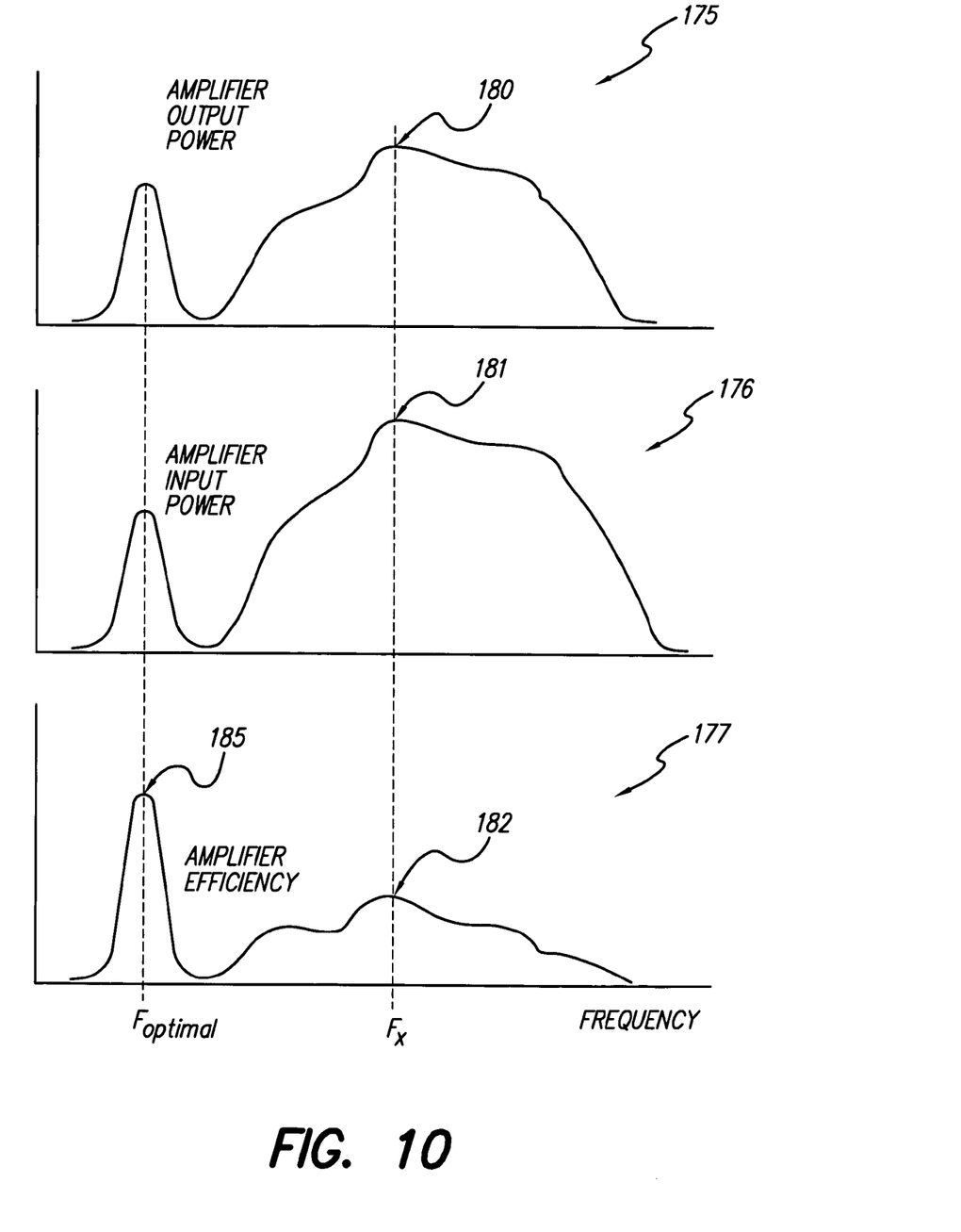
FIG. 10 shows three curves illustrating the relationship between the output power delivered to the antenna/charging coil, the input power into the amplifier, and the efficiency of the amplifier according to principles described herein.

FIG. 10 shows three curves illustrating the relationship between the output power delivered to the antenna/charging coil (34) (curve 175), the amplifier (151) input power (curve 176), and the efficiency of the amplifier (151) (curve 177). As shown in FIG. 10, the output power delivered to the antenna/charging coil (34) may be at a maximum (180) at frequency $F_x$. However, the input power (181) required for the amplifier (151) to deliver the maximum output power (180) to the antenna/charging coil (34) may be very high and may result in an amplifier efficiency that is relatively low (182). If the tuning frequency is adjusted to a high frequency such as $F_x$, excessive heating and damage to the amplifier may result. However, as shown in FIG. 10, an optimal frequency ($F_{optimal}$) may exist wherein the amplifier efficiency is at a maximum (185). By driving the amplifier at $F_{optimal}$, the efficiency of the amplifier (151) may be maximized and the antenna/charging coil (34) may be tuned to the resonant frequency.

Figure 11:
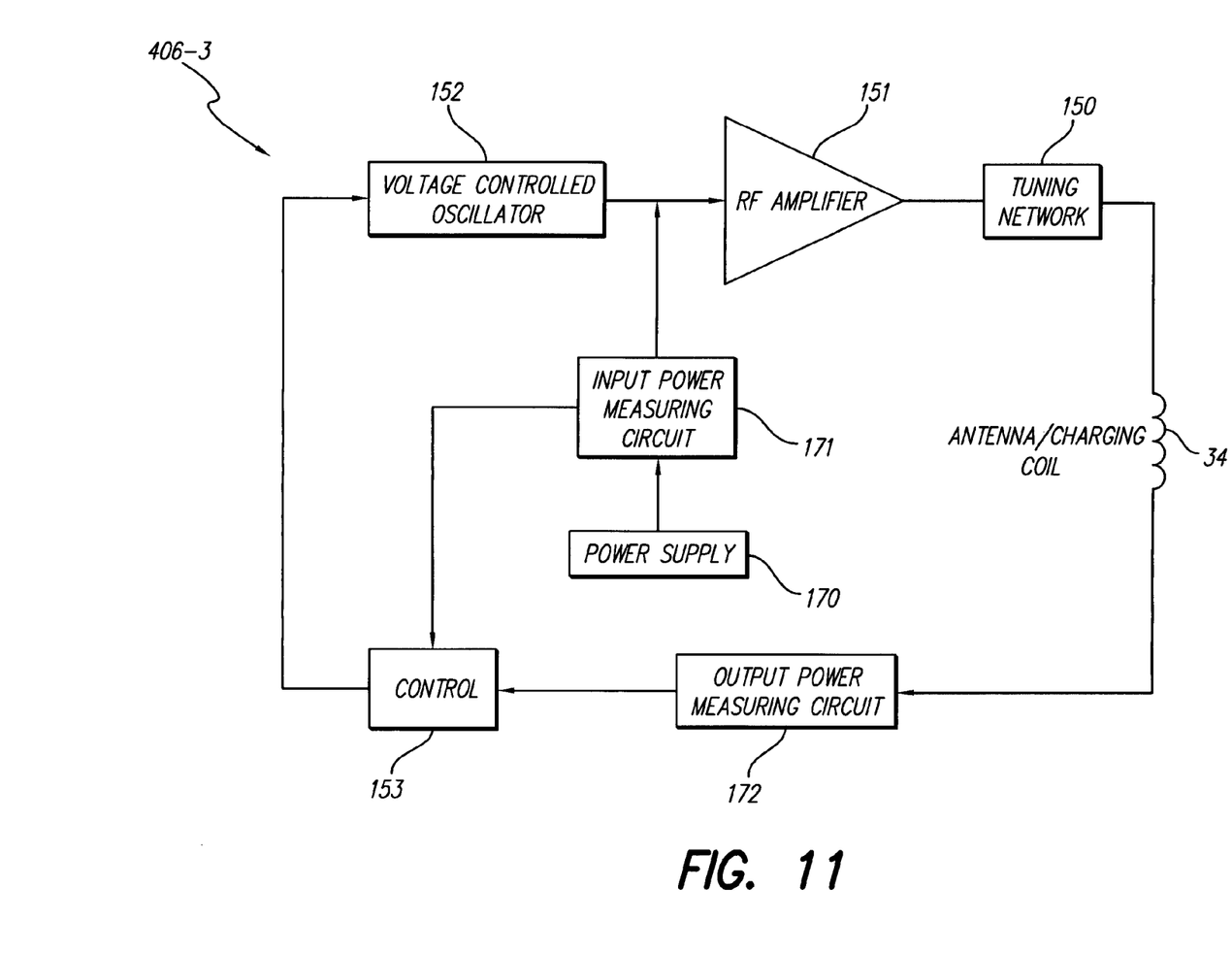
FIG. 11 illustrates an exemplary coil driver circuit configured to adjust the tuning frequency of the antenna/charging coil by maximizing the efficiency of the amplifier according to principles described herein.

FIG. 11 illustrates an exemplary coil driver circuit (406-3) configured to adjust the tuning frequency of the antenna/charging coil (34) by maximizing the efficiency of the amplifier (151) according to one exemplary embodiment. The coil driver circuit (406-3) includes a tuning network (150), an amplifier (151), a voltage controlled oscillator (VCO) (152), a control function (153), a power supply (170) configured to supply input power to the amplifier (151), an output power measuring circuit (172), and an input power measuring circuit (171). The output power measuring circuit (172) is configured to measure the output power of the antenna/charging coil (34) and the input power measuring circuit (171) is configured to measure the power input to the amplifier (151). As shown in FIG. 11, the control function (153) is configured to analyze the output power of the antenna/charging coil (34) and the input power into the amplifier (151) and adjust the frequency output by the VCO (152) such that the efficiency of the amplifier (151) is maximized.

Figure 12:
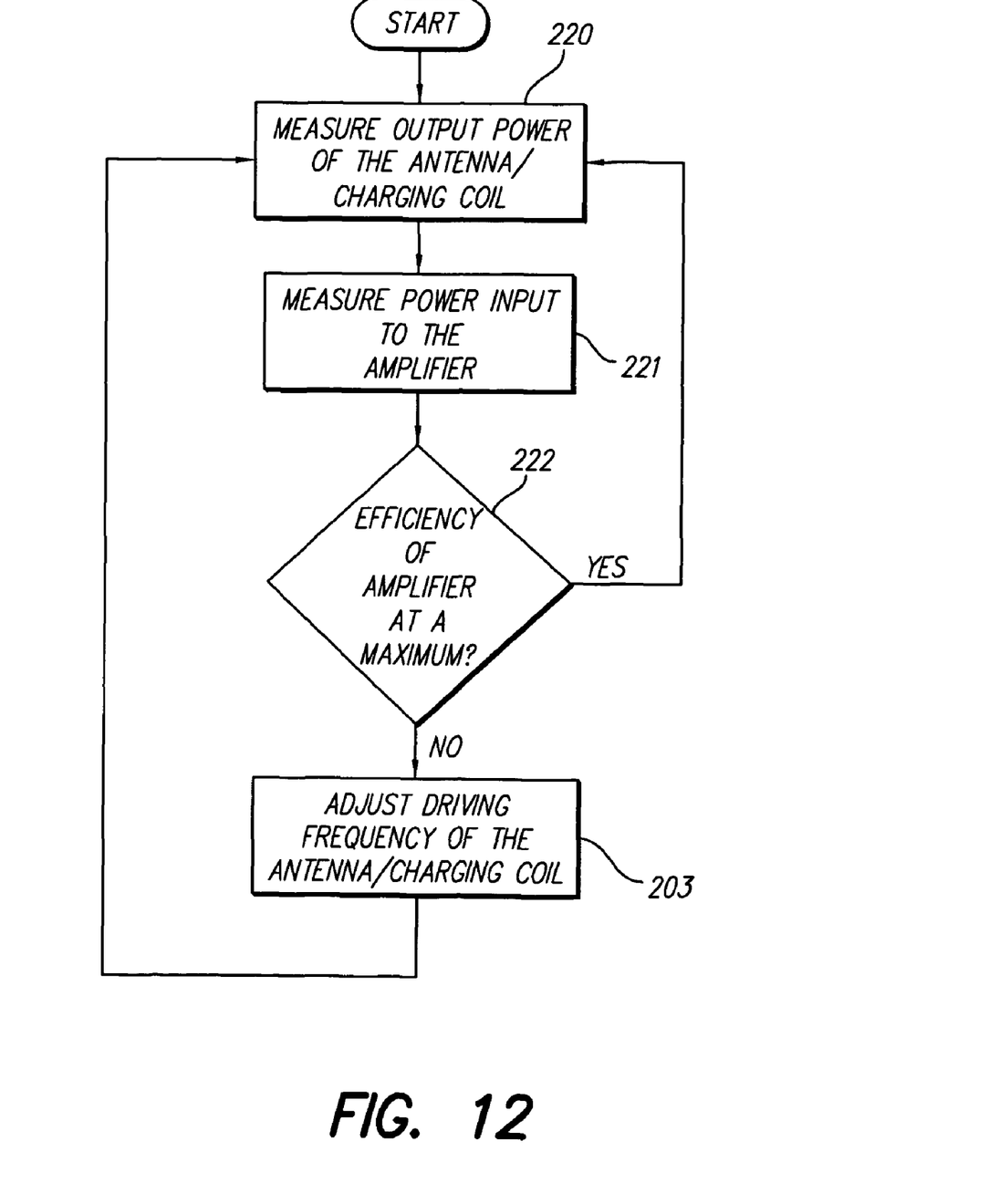
FIG. 12 is a flow chart illustrating a method of tuning the tuning frequency of the antenna/charging coil by maximizing the efficiency of the amplifier.

FIG. 12 is a flow chart illustrating a method of tuning the tuning frequency of the antenna/charging coil (34) by maximizing the efficiency of the amplifier (151). As shown in FIG.

12, the output power of the antenna/charging coil (34) is measured (step 220). The input power into the amplifier (151) is also measured (step 221). The control function (153) may then determine whether the efficiency of the amplifier (151) is at a maximum (step 222). If the efficiency of the amplifier (151) is not maximized (No; step 222), the control function (153) may cause the VCO (152) to adjust the tuning frequency of the antenna/charging coil (34) (step 203). In some embodiments, the tuning frequency is adjusted by decreasing or increasing the frequency of the signal input to the amplifier (151) that drives the antenna/charging coil (34). As shown in FIG. 12, this process may be repeated until the control function (153) determines that the efficiency of the amplifier (151) is maximized (Yes; step 211).

The methods and coil driver circuits described herein for actively adjusting the tuning frequency of the antenna/charging coil (34) may be used to tune any coil included in the external device (20) and/or the internal stimulator (10). For example, the booster coil (411) may be tuned to operate at its resonant frequency using the methods and coil driver circuits described herein.

The preceding description has been presented only to illustrate and describe embodiments of invention. It is not intended to be exhaustive or to limit the invention to any precise form disclosed. Many modifications and variations are possible in light of the above teaching. It is intended that the scope of the invention be defined by the following claims.

What is claimed is:

1. A system for communicating with or providing power to an implantable stimulator, comprising:

a coil configured to emit a magnetic field for driving a corresponding circuit in the implantable stimulator; and
   a coil driver circuit comprising an amplifier for receiving a tuning frequency and for driving the coil with the tuning frequency;
   wherein the coil driver circuit determines the power output of the coil and the power input to the amplifier, and actively adjusts the tuning frequency in response to a ratio of the output power of the coil to the input power to the amplifier.

2. The system of claim 1, wherein the tuning frequency is provided to the amplifier by a voltage controlled oscillator adjusted by the coil driver circuit.

3. The system of claim 1, wherein the coil driver circuit actively adjusts the tuning frequency such that the ratio is maximized.

4. A method of communicating with or providing power to an implantable stimulator, the method comprising:

driving a coil with an amplifier operating at a tuning frequency, the coil emitting a magnetic field used to drive a corresponding circuit in the implantable stimulator; and
   actively adjusting the tuning frequency in response to a comparison between an output power of the coil and an input power into the amplifier.

5. The method of claim 4, wherein the tuning frequency is actively adjusted by a voltage controlled oscillator.

6. The method of claim 4, wherein actively adjusting the tuning frequency comprises maximizing a ratio of the output power of the coil to the input power into the amplifier.

* * * * *